(12) United States Patent
Quijano et al.

(10) Patent No.: US 7,041,132 B2
(45) Date of Patent: May 9, 2006

(54) PERCUTANEOUSLY DELIVERED HEART VALVE AND DELIVERY MEANS THEREOF

(75) Inventors: Rodolfo C. Quijano, Laguna Hills, CA (US); Hosheng Tu, Newport Beach, CA (US)

(73) Assignee: 3F Therapeutics, Inc., Lake Forest, CA (US)

( * ) Notice: Subject to any disclaimer, the term of this patent is extended or adjusted under 35 U.S.C. 154(b) by 0 days.

(21) Appl. No.: 10/222,176

(22) Filed: Aug. 16, 2002

(65) Prior Publication Data

US 2004/0034411 A1 Feb. 19, 2004

(51) Int. Cl.
*A61F 2/06* (2006.01)
(52) U.S. Cl. ..................... 623/2.11; 623/2.17
(58) Field of Classification Search ............... 623/2.11
See application file for complete search history.

(56) References Cited

U.S. PATENT DOCUMENTS

| | | | |
|---|---|---|---|
| 4,261,342 A | 4/1981 | Aranguren Duo | |
| 5,344,442 A | 9/1994 | Deac | |
| 5,350,361 A * | 9/1994 | Tsukashima et al. ... | 604/103.07 |
| 5,411,552 A * | 5/1995 | Andersen et al. ......... | 623/2.18 |
| 5,415,667 A | 5/1995 | Frater | |
| 5,500,015 A | 3/1996 | Deac | |
| 5,554,184 A | 9/1996 | Machiraju | |
| 5,662,704 A | 9/1997 | Gross | |
| 5,824,067 A | 10/1998 | Gross | |
| 5,840,081 A | 11/1998 | Andersen et al. | |
| 5,980,515 A | 11/1999 | Tu | |
| 6,168,614 B1 | 1/2001 | Andersen et al. | |
| 6,270,526 B1 | 8/2001 | Cox | |
| 6,283,127 B1 | 9/2001 | Sterman et al. | |
| 6,733,525 B1 * | 5/2004 | Yang et al. ................ | 623/2.18 |
| 2001/0007856 A1 | 7/2001 | Letac et al. | |

OTHER PUBLICATIONS

The American Heritage Dictionary of the English Language, Third Edition, 1992, Houghton Mifflin Company.*

* cited by examiner

*Primary Examiner*—Thomas Barrett
(74) *Attorney, Agent, or Firm*—Jones Day

(57) ABSTRACT

This invention discloses a percutaneous delivered heart valve and delivery means thereof, wherein the percutaneous delivered heart valve is a twistedly foldable heart valve prosthesis comprising a generally cylindrical support element with a diameter, wherein the support element is twistedly foldable to a smaller diameter, a flexible heart valve with a plurality of valvular leaflets releasably attached to said support element, and a receptacle having a plurality of connecting members secured to the cylindrical support element, wherein the receptacle is releasably matched to an expanding element capable of untwisting the receptacle adapted for un-twisting and unfolding said heart valve.

24 Claims, 8 Drawing Sheets

PERCUTANEOUSLY DELIVERED HEART VALVE AND DELIVERY MEANS THEREOF

FIELD OF THE INVENTION

The invention herein described relates to cardiac atrioventricular valves and minimally invasive delivery systems for using same, specifically to a percutaneously deliverable heart valve suitable for replacement of human heart valve and delivery means thereof.

BACKGROUND OF THE INVENTION

Replacement heart valves have been fabricated or manufactured for the last forty years. Such devices have been assembled from a variety of materials. Specifically the materials have been of biologic or artificial nature, generally leading to two distinct categories of the prostheses as biological or mechanical replacement heart valves.

The prosthetic heart valves are fabricated to replace the natural heart valves that, because of disease, congenital malformations, ageing or trauma have become dysfunctional and require repair to their functional elements or partial or complete replacement. Characteristics for a desirable prosthetic heart valve may include hemodynamic performance, thrombogenicity, durability and ease of surgical implantation.

Human heart valves under the conditions of normal physiological functions are passive devices that open under the pressure of blood flow on their leaflets. There are four valves in the heart that serves to direct the flow of blood through all chambers in a forward direction. In general, blood leaves the heart lower chambers in the direction to the rest of the body or to the lungs for required oxygenation, or blood enters the lower chambers from the upper chambers of the heart. Similarly, they close under the pressure exerted on the same leaflet elements when blood flow is retrograde, thus impeding return of blood flow to the chamber it has just left. This, under normal conditions, (that is, when the body is not under physical stresses and the heart is beating at the normal resting state of about 70 beats per minute) equates to the leaflets opening by separation from each other, thereby producing an opening or closing by apposing to each other approximately 38 million times per year. It can be surmised that under stress conditions this may be happening at higher rates, thus increasing the number of separations and appositions, as well as the forces of impact between the leaflets during the closing.

When disease conditions affect the structure of the materials of the components of the valve apparatus, the valve itself will decay, degenerate or disrupt and require repair or replacement to restore proper function necessary for the continuation of life.

The shape of the leaflet and surrounding elements of a valve or a valve apparatus is dependent on the function of the heart. While in the past numerous publications taught that the preformed valve directs the function, new paradigms have explained that it is the function of the heart that in actuality directs and defines the formation of the specific shape or form of the valve.

In the case of the atrioventricular valves, otherwise known as mitral (in the left lower chamber of the heart) and tricuspid (in the right ventricle), the valve is part of a continuum that extends from the myocardium or muscular wall of the lower chambers, through the papillary muscles, to which is attached a confluence of tendinous rope-like elements known as chordae tendinae that themselves are attached to the edges of differently shaped leaflets which form the flow-allowing and flow-stopping or obstructing elements (leaflets). These leaflets continue and end at a ring-like structure usually known as annulus, that is part of the skeleton of the heart. It is this continuum which should be called an apparatus rather than just valve.

Thus, there is a tricuspid valve apparatus in the right ventricular chamber, and more importantly the mitral valve apparatus within the lower left heart chamber or left ventricle, the pumping function of which provides the systemic flow of blood through the aorta, to keep all tissues of the body supplied with oxygenated blood necessary for cellular function and life. Hence during the cardiac cycle, the valves function as part of a unit composed of multiple interrelated parts, including the ventricular and atria walls, the valve leaflets, the fibrous skeleton of the heart at the atrioventricular ring, and the subvalvular apparatus. The subvalvular apparatus includes the papillary muscle within the ventricle, and the chordae tendinae which connect the papillary muscle to the valve leaflets.

The present practice of valvular surgery when mitral valve alone is replaced after excision of the diseased mitral valve apparatus ignores the necessary contribution of the ventricular function. Ventricle and apparatus work in unison to provide proper pumping to systemic or pulmonary circulation and proper arrest of blood return to the atria chambers.

Aortic and pulmonary valves have been replaced with simple trileaflet chemically treated biological valves obtained from animals, or bileaflet mechanical valves without extreme deficiencies in valvular or cardiac function. This is not the case when mitral or tricuspid valves are replaced and the necessary involvement of chordae tendinae and muscular element of the chamber wall are not united to function in harmony with the valve leaflets. Those valves used in the aortic position cannot alone replace the mitral valve apparatus without anatomical and functional compromise.

Therefore, this requirement to maintain the continuum is of an absolute imperative nature for the mitral or tricuspid valve apparati.

In the past, attempts to generate the needed structure have met with difficulties. Thus, Aranguren Duo in U.S. Pat. No. 4,261,342, Gross in U.S. Pat. No. 5,662,704, and Gross in U.S. Pat. No. 5,824,067, incorporated herein by reference in their entirety, resort to use of a pig heart (porcine, swine) mitral valve to which a covering material is attached to the papillary heads around the chordae tendinae, in the form of a tube that provides an extension in order to fit and affix the valve to the papillary muscle remnants of the human heart after the diseased valve and subvalvular structure is excised and removed from the heart. This tube has to be trimmed until the proper dimension is found to connect the leaflets to the papillary remnants. However, trimming the tube during the surgery is necessary because the relation between annular size and chordal length are different in animal than in human hearts.

Frater in U.S. Pat. No. 5,415,667 teaches an apparatus with a trapezoidal annulus possessing a rigid side. To this trapezoidal annulus are attached four separate leaflets joined together by sutures to provide an occluding surface to the flow of blood during the systolic or ejection phase of the cardiac cycle. The chordae are separate chords attached by sewing to the edge portion of the leaflets though at times are integral of the four separate cusps and each attached by sewing the other three cusps. All four cusps and their respective chordal attachment portions and flange portions are formed as separate components for fitting to a basic ring element having a trapezoidal opening. The sutured attachment portions render the cusp less flexible as compared to a natural cusp without sutures.

Machuraju in U.S. Pat. No. 5,554,184 discloses cutting two leaflets that are then sutured together to form a bileaflet valve. Similarly, Deac in U.S. Pat. No. 5,344,442 and U.S. Pat. No. 5,500,015, entire disclosures of which are incorporated herein by reference, teaches means for cutting sections of biological material and joins them by sutures to form a bileaflet mitral valve. The sutured joint portion becomes stiff and less flexible. There is a clinical needs to fabricate a bileaflet or trileaflet valve with sutureless joint portion or commissure; preferably to have the valve made from a singular membrane of tissue or artificial sheet.

All of the aforementioned patents teach of a form made by stitching various sections of material and expecting that the form will be able to profile the function. This leads Cox in U.S. Pat. No. 6,270,526 to pronounce his principle of "Form Follows Function". He notices that the human foetus while in its early stages (about 25 days of gestation) in utero that further exhibits tubular connections between the foetal heart gestational developments will produce the structure. This "Form Follows Function" is the paradigm that must be used in order to fabricate a heart valve that will very closely identify with the human heart valve.

Under the best of circumstances (i.e., replacement of the aortic valve), the construction of artificial tissue valves has been based on the concept that if the artificial valve can be made to approximate the anatomy (form) of the native valve, then the physiology (function) of the artificial valve will also approximate that of the native valve. This is the concept that "Function Follows Form." For example, the manufacturers of all artificial porcine valves first re-create the form of a native human aortic valve by: 1) harvesting a porcine aortic valve, 2) fixing it in glutaraldehyde or other suitable fixatives to eliminate antigenicity, and 3) suturing the porcine valve to a stent to hold the three leaflets in place. In other words, the primary goal in the construction of these artificial valves is to reproduce the form of the human aortic valve as closely as possible. The assumption is made that if the artificial valve can be made to look like the human aortic valve, it will function like the human aortic valve (i.e., proper function will follow proper form). The same assumption is also followed for commercially available pericardial valves.

Current Options for Tissue Heart Valve Replacement

Most tissue valves are constructed by sewing the leaflets of pig aortic valves to a stent to hold the leaflets in proper position as a stented porcine valve. They may also be constructed by removing valve leaflets from the pericardial sac of cows or horses and sewing them to a stent as a stented pericardium valve. The stents may be rigid or slightly flexible and covered with cloth (usually a synthetic material sold under the trademark Dacron™ or Teflon™) and attached to a sewing ring for fixation to the patient's native tissue. In one embodiment, the porcine, bovine or equine tissue is chemically treated to alleviate any antigenicity.

A stentless valve prosthesis generally comprises a biological valve having a suture ring, anchoring skirts at the commissures of the valve, and an outer polyester covering. A stentless valve prosthesis secured to the native valve annulus and leaflets reduces tissue stress as the flexible valve prosthesis adapted and conforms to the native valve, so that durability and resistance to wear and calcification are improved.

The main advantage of tissue valves is that they do not cause blood clots to form as readily as do the mechanical valves, and therefore, the tissue valves do not typically require life-long systemic anticoagulation. Another advantage is that tissue valve is so flexible that it can be shaped and configured for delivery percutaneously. However, the presence of the stent and sewing ring prevents the tissue valve from being anatomically accurate in comparison to a normal heart valve.

Principles of Tissue Heart Valve Construction

In co-pending patent applications, a supportless tissue valve is disclosed following the principles of the "function follows form" principles of tissue heart valve construction, as taught by Cox in U.S. Pat. No. 6,270,526, No. 6,092,529, No. 5,824,063, No. 5,713,950, and No. 5,480,424, all incorporated herein by reference in their entirety. The co-pending patent applications Ser. No. 10/137,637 filed May 2, 2002, entitled "Supportless atrioventricular heart valve and minimally invasive delivery system thereof" and Ser. No. 10/086,100 filed Feb. 28, 2002, entitled "Stentless atrioventricular heart valve fabricated from a singular flat membrane", entire contents of both applications being incorporated herein by reference, teach a heart valve and its percutaneous delivery means.

Although homograft (human cadaver) and porcine aortic valves have the gross appearance of native aortic valves, the fixation process (freezing with liquid nitrogen, and chemical treatment, respectively) alters the histological (microscopic) characteristics of the valve tissue. Porcine and bovine pericardial valves not only require chemical preparation (usually involving fixation with glutaraldehyde), but the leaflets must be sutured to cloth-covered stents in order to hold the leaflets in position for proper opening and closing of the valve. A recent advance has been made in this regard by using "stentless" porcine valves that are sutured directly to the patient's native tissues for aortic valve replacement, but the problem of chemical fixation remains. In addition, these stentless artificial valves cannot be used for mitral or tricuspid valve replacement.

Percutaneous Catheter-based Delivery

Andersen et al. in U.S. Pat. No. 6,168,614, entire contents of which are incorporated herein by reference, discloses a heart valve prosthesis for implantation in the body by use of a catheter. The valve prosthesis is consisted of a support structure with a tissue valve connected to it, wherein the support structure is delivered in a collapsed shape through a blood vessel and secured to a desired valve location with the support structure in the expanded shape.

Andersen et al. in U.S. Pat. No. 5,840,081 and No. 5,411,552, entire contents of both of which are incorporated herein by reference, discloses a system for implanting a valve in a body channel comprising a radially collapsible and expandable stent with a valve mounted to it and a catheter for introducing and securing the valve in the body channel. The catheter generally comprises an expandable member about which the cylindrical stent may be positioned together with the valve, fastening means on the expandable member on which the stent may be mounted to the expandable member, and a channel extending through the catheter for injecting a fluid into the expandable member so as to expand the expandable member from a collapsed profile suitable for introduction into the body channel to an expanded profile in which the stent engages the inner wall of the body channel so as to secure the valve therein.

It is one aspect of the present invention to provide a percutaneously deliverable heart valve that is expandable by an un-twist mechanism releasably mounted with and secured to the support element of the implantable heart valve prosthesis.

Percutaneous Intercostal Delivery

Various surgical techniques may be used to repair a diseased or damaged valve, including annuloplasty (contracting the valve annulus), quadrangular resection (narrowing the valve leaflets), commissurotomy (cutting the valve commissures to separate the valve leaflets), shortening mitral or tricuspid valve chordae tendinae, reattachment of severed atrioventricular valve chordae tendinae or papillary muscle tissue, and decalcification of valve and annulus tissue. Alternatively, the valve may be replaced, by excising the valve leaflets of the natural valve, and securing a replacement valve in the valve position, usually by suturing the replacement valve to the natural valve annulus.

A conventional procedure for approaching the left atrium is by intravascular catheterization from a femoral vein through the cardiac septal which separates the right atrium and the left atrium. This intravascular procedure is not only dangerous and tedious because of long tortuous route, but also limited use because of the catheter size suitable for insertion intravascularly.

Sterman et al. in U.S. Pat. No. 6,283,127, entire contents of which are incorporated herein by reference, discloses a device system and methods facilitating intervention within the heart or great vessels without the need for a median sternotomy or other form of gross thoracotomy, substantially reducing trauma, risk of complication, recovery time, and pain for the patient. Using the device systems and methods of the invention, surgical procedures may be performed through percutaneous penetrations within intercostal spaces of the patient's rib cage, without cutting, removing, or significantly displacing any of the patient's ribs or sternum. The device systems and methods are particularly well adapted for heart valve repair and replacement, facilitating visualization within the patient's thoracic cavity, repair or removal of the patient's natural valve, and, if necessary, attachment of a replacement valve in the natural valve position.

Of particular interest in the present application are techniques for the implantation of an atrioventricular valve that can be retracted or folded inside a delivery system or cannula for delivering through a less invasive intercostal penetration to the desired place, particularly in a left atrium. Thereafter the retracted valve is released, expanded, separated from the delivery system, and secured to the desired place with a minimally invasive technique. The same minimally invasive system can also deliver a medical device for drug delivery, energy delivery, and tissue ablation, among other applications.

Therefore, it would be desirable to provide a delivery system for delivering therapeutic means in a patient's heart comprising a heart valve configured to be releasably folded inside a lumen of the delivery system through a percutaneous intercostal penetration of a patient's chest or an opening at a carotid artery, jugular vein, subclavian vein, femoral vein and other blood vessel.

Another object of the present invention is to fabricate a heart valve prosthesis comprising a supportless atrioventricular valve releasably secured to a twistedly foldable support element and a delivery system thereof that avoids the afore-mentioned disadvantages, wherein the supportless valve comprises a singular membrane of biocompatible material that has at least two cusps configured to form a substantially tubular shape for use as an atrioventricular valve, and wherein the delivery system comprises a short apparatus for approaching the left atrium through a percutaneous intercostal penetration or through an opening at a carotid artery, jugular vein, subclavian vein, femoral vein and other blood vessel.

SUMMARY OF THE INVENTION

It is one object of the present invention to provide a supportless and/or stentless atrioventricular valve comprising a singular membrane of tissue or plastic material. In one embodiment, the valve has a sewing ring and at least two cusps hinged continuously from the inner opening of the sewing ring, wherein the cusps are an integral part of a continuum from the singular membrane configured or conformed to form a substantially tubular shape for use as an atrioventricular valve. In another embodiment, the substantially tubular form of the disclosed supportless atrioventricular valve follows the "Function Follows Form" concept.

It is another object of the present invention to fabricate a supportless atrioventricular valve with a singular membrane of tissue material that is chemically treated to reduce its antigenicity. In some aspect of the present invention, the tissue material is pericardium tissue selected from a group consisting of equine, bovine, porcine, and ovine. Alternately, the singular membrane of material of the present invention is a synthetic plastic selected from a polymer group consisting of silicone, polyurethane, latex, and mixture thereof.

It is still another object of the present invention to provide a method of forming a supportless atrioventricular valve intended for attaching to a circumferential valve ring and papillary muscles of a patient comprising a singular membrane of biomaterial with at least two cusps, wherein either cusp has a semicircular tip edge joined by two generally straight side edges and wherein each straight side edge is trimmed and configured at an angle of about less than 20 degrees from a reference imaginary central longitudinal line of that cusp.

It is a preferred object of the present invention to provide a delivery system and methods for minimally invasively delivering a foldable heart valve prosthesis into anterior of a patient heart. In one embodiment, the delivery system has a differentially expandable balloon on the balloon catheter that is configured to expand the circularly folded valve into an oval deployed valve, wherein the differentially expandable balloon comprises a longitudinal axis, a major traverse axis and a minor traverse axis, the major traverse axis being at least 10% longer than the minor traverse axis.

It is therefore an object of the present invention to provide a method for minimally invasively delivering a foldable heart valve prosthesis into a patient, the foldable heart valve prosthesis comprising a twistedly foldable support element and a heart valve releasably secured to the support element. In some aspect of the present invention, the method comprises the steps of: twistedly folding the support element with the secured heart valve within a lumen of a delivery apparatus; delivering the delivery apparatus to a target valvular annulus of the patient; un-twisting the support element to unfold and deploy the heart valve in place; and removing the support element after the un-twisting step.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Referring to FIGS. 1 to 8, what is shown is an embodiment of a percutaneously delivered heart valve and delivery means thereof, including a supportless and stentless atrioventricular valve comprising a singular membrane of tissue or plastic biomaterial. While the description sets forth various embodiment specific details, it will be appreciated that the description is illustrative only and should not to be construed in any way as limiting the invention. Furthermore, various applications of the invention, and modifications thereto, which may occur to those who are skilled in the art, are also encompassed by the general concepts described below.

Percutaneous Heart Valve Delivery

Andersen et al. in U.S. Pat. No. 6,168,614, No. 5,840,081 and No. 5,411,552 discloses a valve prosthesis for implantation in the body by use of catheter comprising a stent made from an expandable cylinder-shaped thread structure comprising several spaced apices. The elastically collapsible valve is mounted on the stent as the commissural points of the valve and is secured to the projecting apices. The valve prosthesis can be compressed around the balloon means of the balloon catheter and be inserted in a channel, for instance in the aorta. When the valve prosthesis is placed correctly, the balloon means is inflated thereby expanding the stent and wedging it against the wall of the aorta. The balloon means is provided with beads to ensure a steady fastening of the valve prosthesis on the balloon means during insertion and expansion. However, a tissue valve compressed by a balloon as taught by Andersen et al. tends to become dehydrated undesirably and hence may cause long-term calcification problems.

Letac et al. in U.S. patent application Ser. No. 2001/0007956, entire contents of which are incorporated herein by reference, discloses a valve prosthesis for implantation in a body channel comprising a collapsible valvular structure and an expandable frame on which the valvular structure is mounted. The valvular structure is composed of a valvular tissue compatible with the human body and blood, the valvular tissue being sufficiently supple and resistant to allow the valvular structure to be deformed from a closed state to an opened state. The valvular tissue forms a continuous surface and is provided with guiding means formed or incorporated within, said guiding means creating stiffened zones which induce the valvular structure to follow a patterned movement in its expansion to its opened state and in its turning back to its closed state. However, the valvular tissue compressed by a balloon as taught by Letac et al. tends to become undesirably dehydrated and hence may cause long-term calcification problems.

Figure 1:
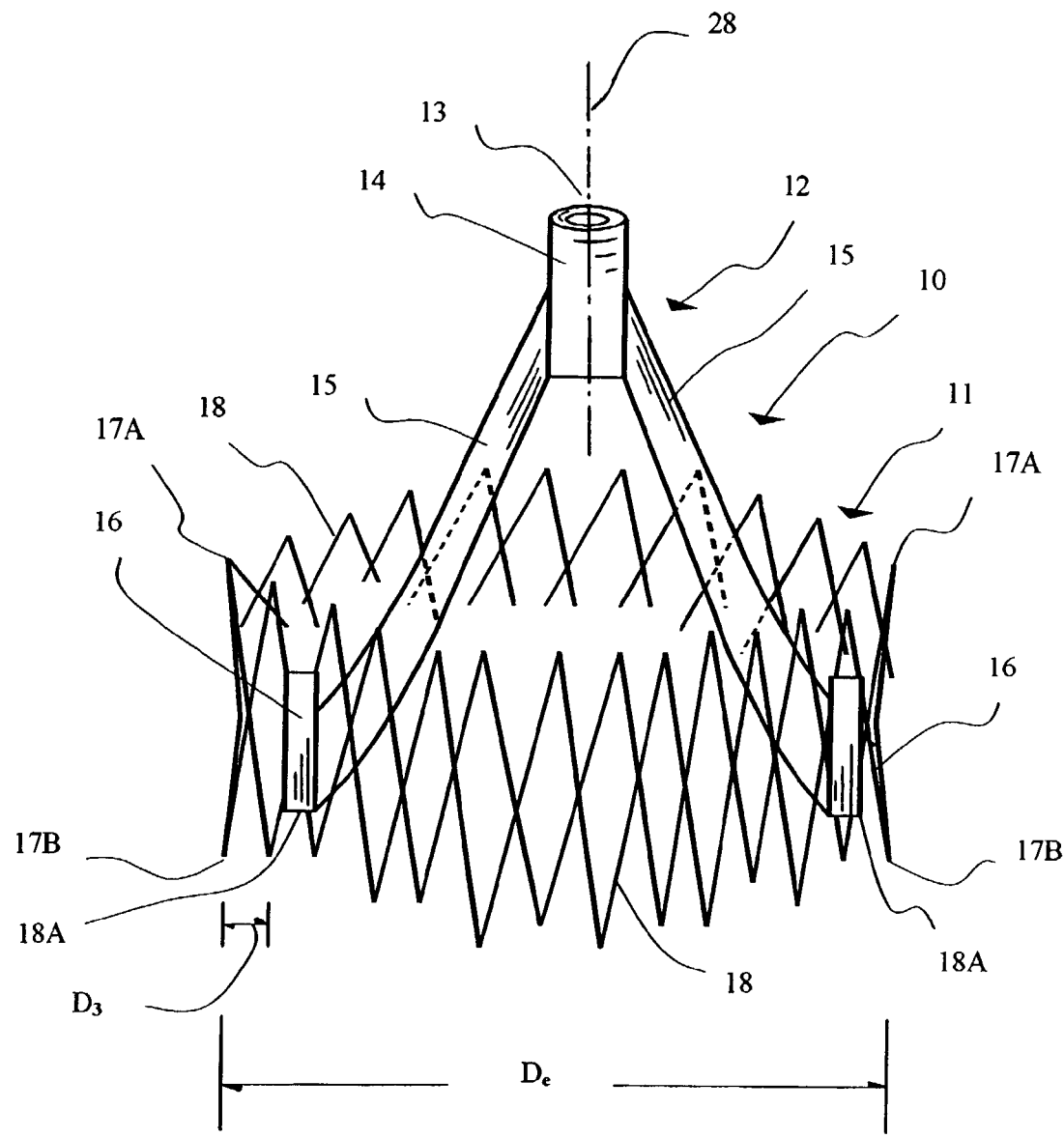
FIG. 1 is a twistedly foldable heart valve prosthesis comprising a generally cylindrical support element at a fully unfolded state in accordance with one embodiment of the present invention.

FIG. 1 shows an example illustrating a twistedly foldable heart valve prosthesis comprising a generally cylindrical support element 11 at a fully unfolding state in accordance with one embodiment of the present invention. The term "untwist" is intended herein to mean an action that enlarges the circumference of a generally cylindrical support folded element by unturning or unwinding in a clockwise or counter-clockwise rotation so as to deploy the folded support element. In one aspect of the present invention, the support element 11 may be made of an expandable metallic frame with intercrossing linear bars 18 configuration or other suitable configurations. The height of the linear bars 18 is configured in a proper length sufficient to support a valvular structure or a heart valve. The cross-sectional diameter of the support element 11 is preferred to be about a few millimeters at a folded state to about 10 mm or larger at a fully unfolded state. The number and size of the bars 18 are adapted to be sufficiently strong and rigid when the support element is fully open in the valvular orifice to resist the strong recoil force exerted by the distorted stenosed valve orifice after untwisting the support element used in the delivery technique to enlarge the stenosed valve orifice.

The twistedly foldable heart valve prosthesis of the present invention is intended to replace a diseased valve of a patient. The valve prosthesis 10 may comprise: a generally cylindrical support element 11 with a diameter, wherein the support element is twistedly foldable to a smaller diameter; a flexible heart valve with a plurality of valvular leaflets releasably attached to the support element; and a receptacle 14 having a plurality of connecting members secured to the cylindrical support element, wherein the receptacle is releasably matched to an expanding element capable of untwisting the receptacle adapted for un-twisting and unfolding the heart valve.

The twistedly foldable heart valve prosthesis 10 may further comprise a twist mechanism 12 which is releasably secured to the generally cylindrical support element 11. The twist mechanism 12 comprises a receptacle or coupler 14 with an engaging thread 13, wherein the engaging thread 13 is matchable to a corresponding thread 32 of the expanding element, for example, a handpiece 41 or a delivery apparatus 31, for untwisting the twist mechanism 12 to unfold the cylindrical support 11. The twist mechanism 12 may further comprise a plurality of connecting members 15 and connecting bars 16, wherein one end of the connecting member 15 is secured to the coupler 14 and the opposite end is secured to the connecting bars 16. The connecting members 15 are made of a sturdy, high torque material so as to enable untwisting the cylindrical support 11 against the strong recoil force exerted by the distorted stenosed valve orifice.

The connecting bars 16 are secured to the intercrossing bars 18A of the support element 11 either releasably or permanently. In one embodiment, those intercrossing bars 18A involved with coupling to the connecting bars 16 are configured to have a trough or track so as to enable the connecting bars 16 to securely ride into the trough or track. For releasing the connecting bars 16 from those intercrossing bars 18A, the connecting bars 16 could be slid out of the trough or track of the intercrossing bars 18A. The connecting bars 16 are made of a biocompatible metallic material, sized and configured to minimize affecting the mounting and/or the function of the valvular structure. In one embodiment, the connecting bars 16 are coupled to the intercrossing bars 18A securely with an appropriate manner and at a proper location of the intercrossing bars 18A so as to untwist the cylindrical support 11 essentially uniformly across all the intercrossing bars 18A.

Figure 2:
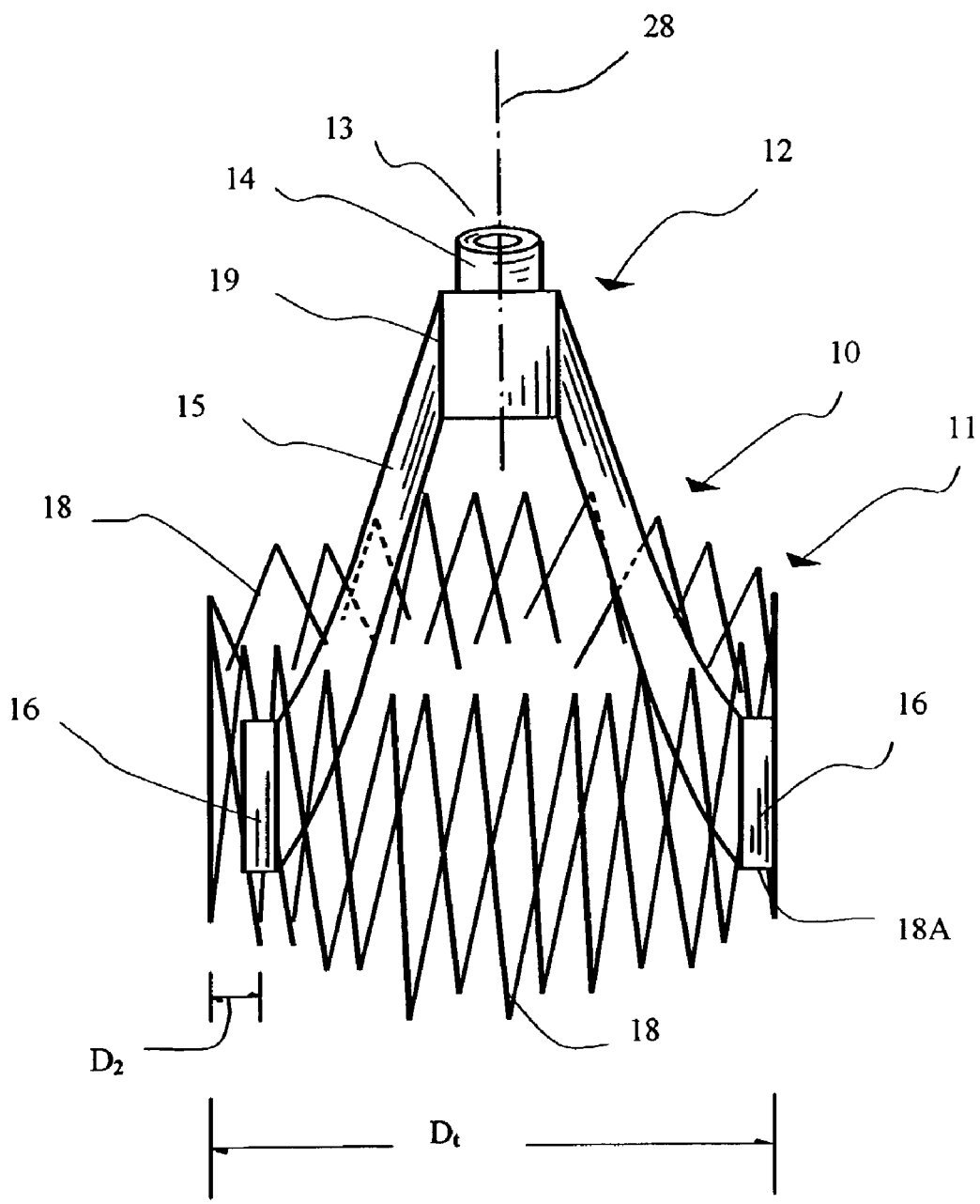
FIG. 2 is a twistedly foldable heart valve prosthesis of FIG. 1 comprising a generally cylindrical support element at a semi-unfolded state.
Figure 3:
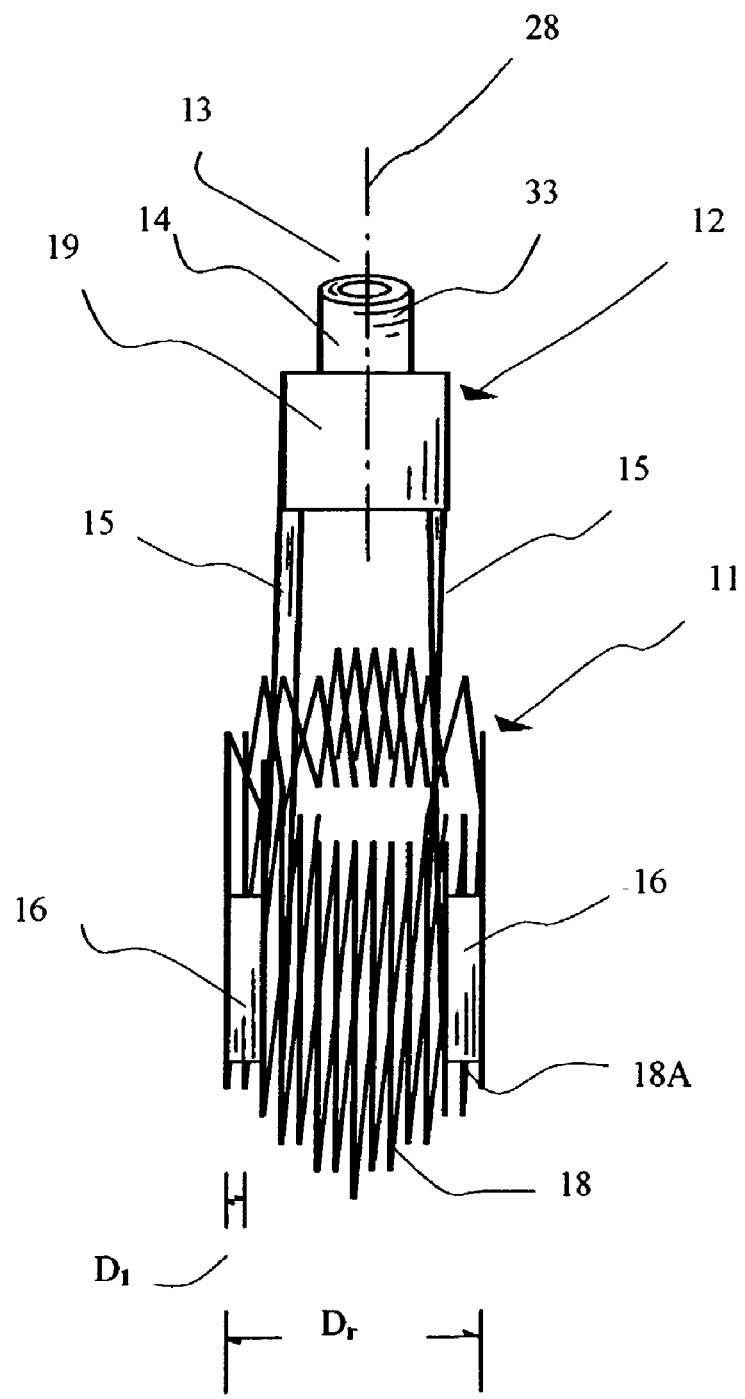
FIG. 3 is a twistedly foldable heart valve prosthesis of FIG. 1 comprising a generally cylindrical support element at a folded state.

For illustration purposes, the spaced apart distance between any two intercrossing bars 18 is designed as $D_3$ when the support element is fully unfolded, wherein the corresponding diameter of the support element 11 is designated as $D_e$ (FIG. 1). As shown in FIG. 2, the spaced apart distance between any two intercrossing bars 18 is designed as $D_2$ when the support element 11 is semi unfolded, wherein the corresponding diameter of the support element 11 is designated as $D_f$. FIG. 3 shows the spaced apart distance between any two intercrossing bars 18 designed as $D_1$ and the corresponding diameter of the support element 11 designated as $D_r$, when the support element 11 is folded. According to the principles of the present invention, the relationship for the spaced distances is as follows: $D_1 < D_2 < D_3$. Correspondingly, the relationship for the diameters of the support element 11 is as follows: $D_r < D_f < D_e$.

FIG. 2 shows a twistedly foldable heart valve prosthesis 10 of FIG. 1 comprising a generally cylindrical support element 11 at a semi-unfolded state. The support element 11 is generally symmetric with respect to an imaginary central axial line 28 of the support element, when the support element 11 is semi unfolded or fully unfolded by the twist mechanism 12. As well known to an ordinary artisan skilled in the art, a portion 19 of the twisted connecting members 15 accumulates on the coupler or receptacle 14.

FIG. 3 shows a twistedly foldable heart valve prosthesis of FIG. 1 comprising a generally cylindrical support element 11 at a folded state suitable for percutaneous delivery by a delivery apparatus, such as a catheter, a cannula or an endoscopic instrument. The intercrossing bars 18 according to the principles of the present invention are configured and sized to be flexible longitudinally for easy delivery passing the tortuous natural conduits or openings. However, the intercrossing bars 18 have adequate hoop strength (that is, the strength in an outwardly radial direction of the circular support element) to expand the valvular annulus and resist the strong recoil force exerted by the distorted stenosed valve orifice after untwisting the support element 11 used in the delivery means to enlarge the stenosed valve orifice.

In some aspect of the present invention, after fully unfolding the support element 11, the intercrossing bars 18 was configured pre-shaped to exhibit at least a slightly outwardly pointed joint as an anchoring member 17A or 17B, formed of any two intercrossing bars so as to anchor the heart valve prosthesis 10 securely into the annular tissue of the patient. The angle of the first anchoring member 17A with respect to an imaginary axial line 28 of the support may be different from that of the second anchoring member 17B. It is one aspect of the present invention to provide a heart valve prosthesis, wherein the cylindrical support element 11 further comprises a plurality of anchoring members 17A, 17B for anchoring the support element onto annular tissue of the diseased valve, and wherein the anchoring members are triggered facing outwardly when the support element 11 is fully untwisted.

Figure 4:
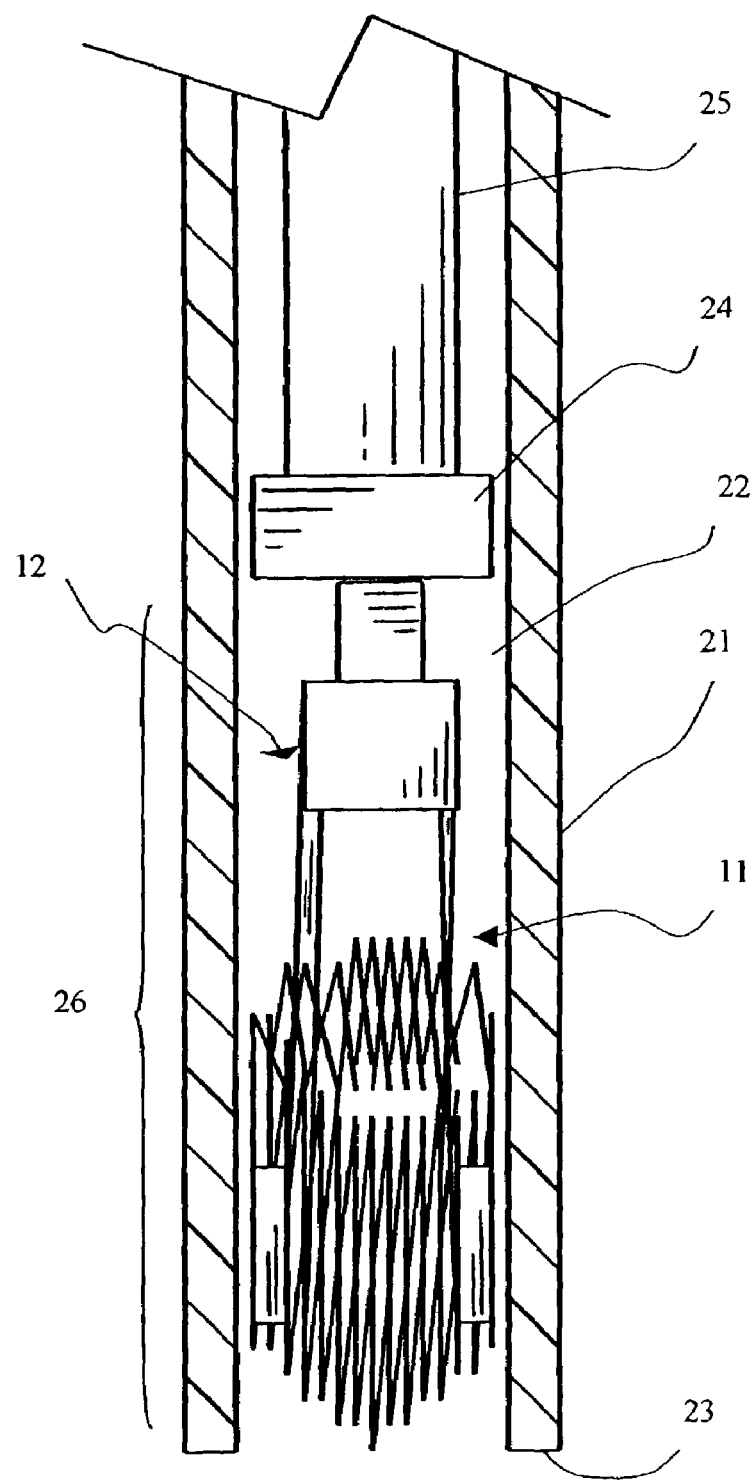
FIG. 4 is a cross-sectional view of a delivery apparatus enclosing a twistedly foldable heart valve prosthesis comprising a generally cylindrical support element at a folded state.

FIG. 4 shows a cross-sectional view of a delivery apparatus enclosing a twistedly foldable heart valve prosthesis comprising a generally cylindrical support element at a folded state. In one embodiment, the delivery apparatus may comprise a catheter, wherein the catheter passes through an opening at a carotid artery, a jugular vein, a subclavian vein, or any body vessel. In another embodiment, the delivery apparatus may comprise a cannula, the cannula passing through a percutaneous intercostal penetration.

Figure 8:
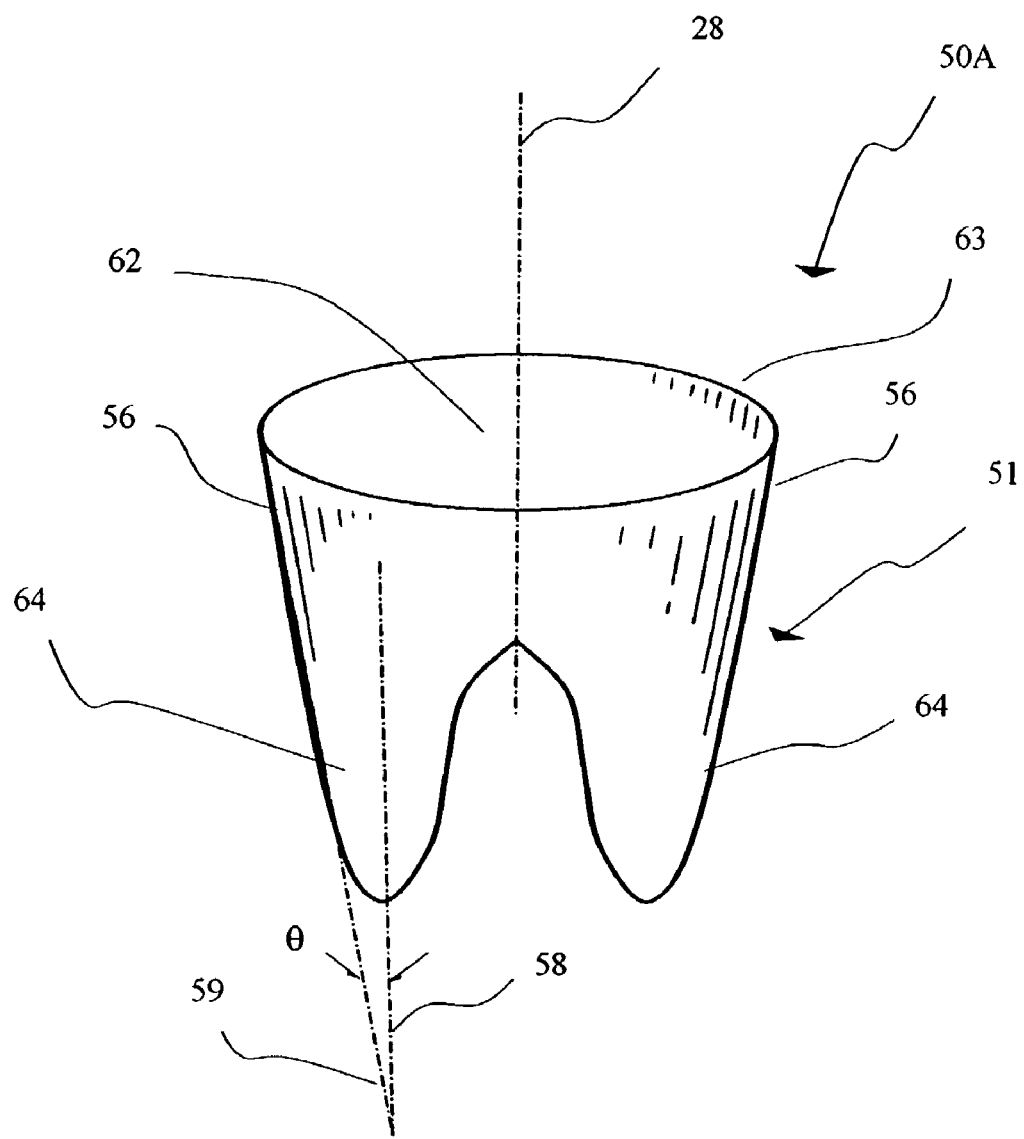
FIG. 8 is a perspective view of a twistedly foldable atrioventricular heart valve prosthesis at a fully unfolding state after releasing the generally cylindrical removable support element.

It is some aspect of the present invention to provide a method for minimally invasively delivering a foldable heart valve prosthesis 10 into a patient, the foldable heart valve prosthesis comprising a twistedly foldable support element 11 and a heart valve, for example, an atrioventricular valve 51 in FIG. 8, releasably secured to the support element 11. The method may comprise the steps of: twistedly folding the support element with the secured heart valve within a lumen of a delivery apparatus; delivering the delivery apparatus to a target valvular annulus of the patient; and un-twisting the support element to unfold and deploy the heart valve in place. In one embodiment, the method may further comprise a step for removing the support element after the un-twisting step.

In one embodiment, the method may further comprise a step of removing at least a portion of a patient's heart valve by means of a cutting tool introduced through the percutaneous intercostal penetration and through an internal penetration on a cardiac wall before the twistedly folding step. In some aspect of the present invention, the cutting tool may be made of an electrically conductive metal and radiofrequency energy is provided to the cutting tool for enhanced valve removal. The high frequency energy ablation is well known to an ordinary artisan who is skilled in the art. One example of using radiofrequency energy in cutting a tissue 3 is shown in U.S. Pat. No. 5,980,515 entitled "Devices and Methods for lead extraction", incorporated herein by reference.

The method may further comprise a step of fastening the unfolded heart valve within the valvular annulus by means of an instrument introduced through the percutaneous intercostal penetration and through an internal penetration on a cardiac wall after the un-twisting step. The process of removing at least a portion of a patient's heart valve by means of a cutting tool and the process of fastening the unfolded heart valve within the valvular annulus by means of an instrument introduced through the percutaneous intercostal penetration and through an internal penetration on a cardiac wall is well know to one ordinary artisan who is skilled in the art.

The delivery apparatus 21 comprises a distal section 26, a distal end 23 and a lumen 22, wherein a device deployment mechanism 25 with a plunger 24 is located within the lumen 22 of the delivery apparatus 21. The twistedly foldable heart valve prosthesis in its folded state stays inside the lumen of the delivery apparatus 21 as shown in FIG. 4 during the delivery phase through an intercostal penetration or through an opening of the blood vessel.

Figure 5:
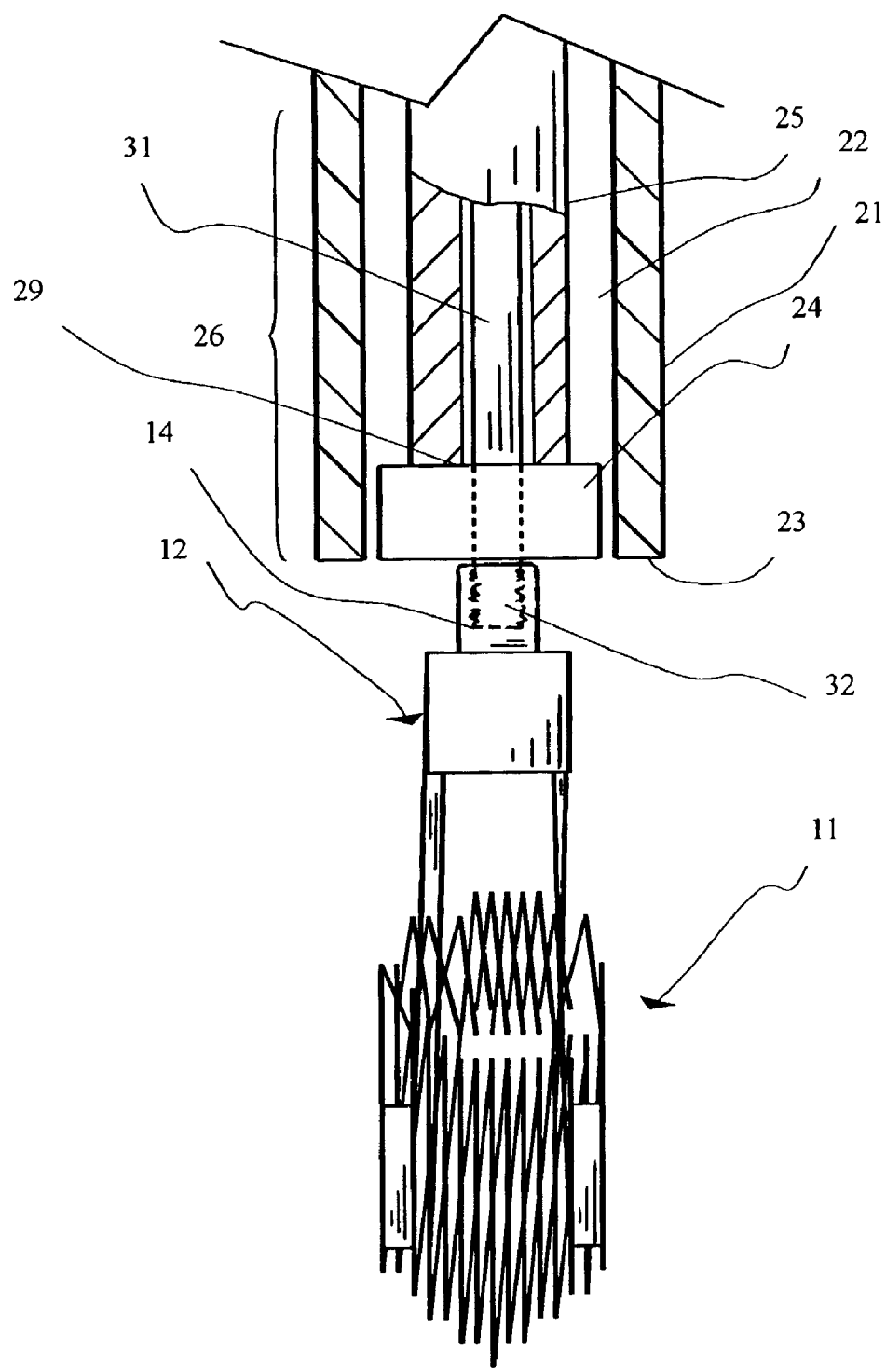
FIG. 5 is a first step for delivering a twistedly foldable heart valve prosthesis at a folded state out of the delivery apparatus.

Once the distal section of the delivery apparatus arrives at an appropriate location adjacent the valvular annulus of the diseased heart valve, the twistedly foldable heart valve prosthesis is pushed out of the distal end 23 of the delivery apparatus 21 (shown in FIG. 5). The delivery apparatus may further comprise an expanding element, for example, a handpiece 41 or an engaging element 31, both having a corresponding thread 32 for matching and untwisting the twist mechanism 12 to unfold the cylindrical support element 11. In one embodiment in FIG. 5, the engaging element 31 passes through a throughput opening 29 on the plunger 24 to engage with the engaging thread 13 of the receptacle 14, wherein the engaging thread 13 is matchable to the corresponding thread 32 of the engaging element 31 or the handpiece 41.

Figure 6:
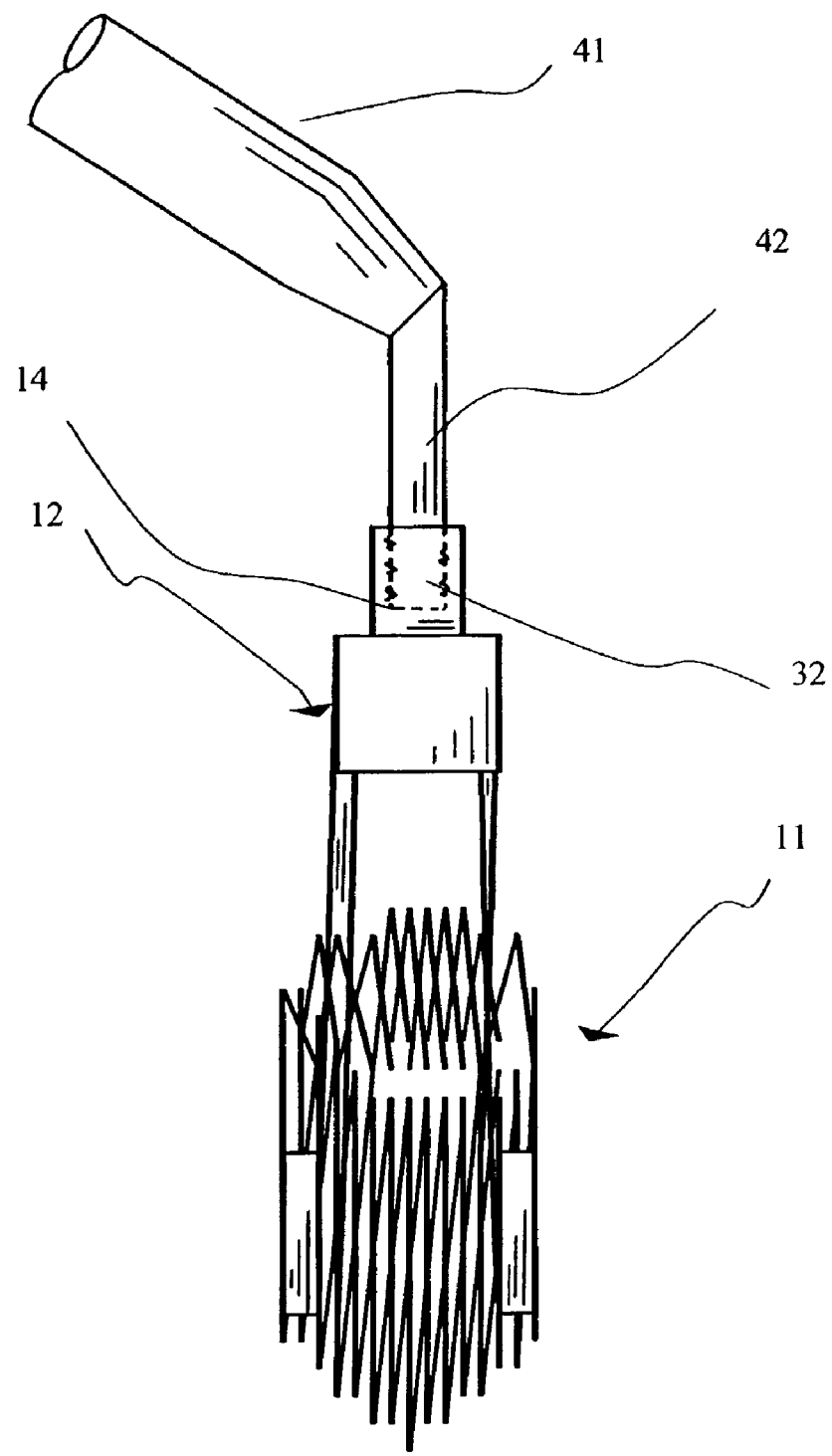
FIG. 6 is one deploying means for unfolding a twistedly foldable heart valve prosthesis comprising a generally cylindrical support element at a folded state.

FIG. 6 shows one deployment means with a handpiece 41 with a twisting means 42 having a corresponding thread 32 at its distal end for unfolding a twistedly foldable heart valve prosthesis comprising a generally cylindrical support element 11 at a folded state. The handpiece can be applied after the twistedly foldable heart valve prosthesis has been delivered to the target position and temporarily held in place. The handpiece can be inserted through an intercostal penetration or used as a part of other deployment means. To apply some frictional force on the support element 11 enabling for untwisting the folded support element 11, the support element can be placed against any valvular tissue for an effective untwisting action.

Figure 7:
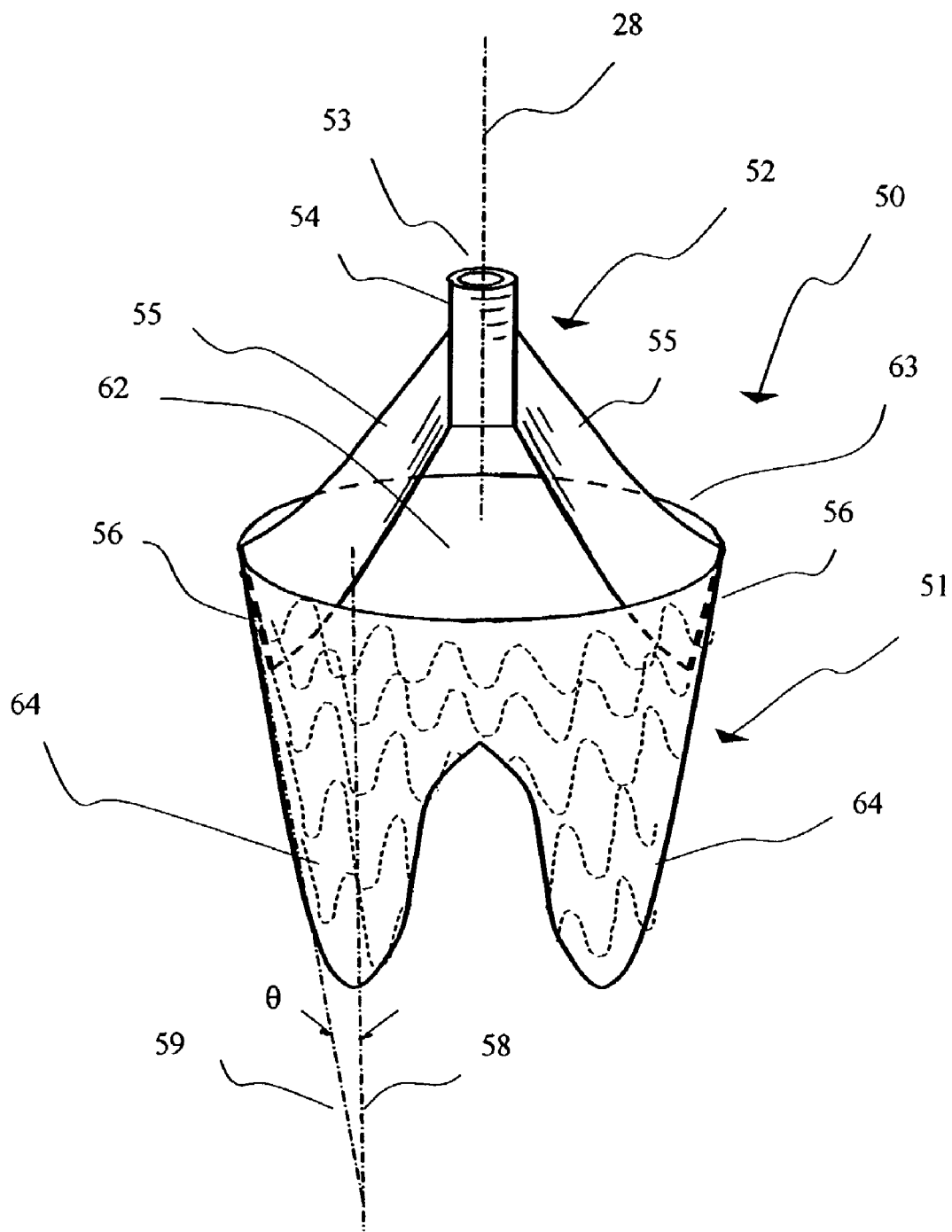
FIG. 7 is a perspective view of a twistedly foldable atrioventricular heart valve prosthesis comprising a generally cylindrical removable support element at a fully unfolding state.

FIG. 7 shows a perspective view of a twistedly foldable atrioventricular heart valve prosthesis 50 comprising a twist mechanism 52 which is releasably secured to the generally cylindrical support element 51 with tissue cusps 64 secured to the support element 51 at a fully unfolded state. The twist mechanism 52 may comprise a receptacle 54 with an engaging thread 53, wherein the engaging thread 53 is matchable to a corresponding thread of any expanding element, for example, a handpiece 41 or an engaging element 31, for untwisting the twist mechanism 52 to unfold the cylindrical support 51 along with the secured tissue cusps 64. The twist mechanism 52 may further comprise a plurality of connecting members 55 and connecting bars 56, wherein one end of the connecting member 55 is secured to the receptacle 54 and the opposite end is secured to the connecting bars 56. The connecting members 55 are made of a sturdy, high torque material so as to enable untwisting the cylindrical support 51 against the strong recoil force exerted by the distorted stenosed valve orifice.

It is one object of the present invention to provide a twistedly foldable heart valve prosthesis to replace a diseased valve of a patient. The diseased heart valve may be selected from a group consisting of an aortic valve, a pulmonary valve, and an atrioventricular valve of mitral or tricuspid valves. The foldable heart valve prosthesis is usually folded to be within a delivery catheter of about less than 24 French, corresponding to about 8 mm. The heart valve prosthesis may comprise (a) a generally cylindrical support element with a diameter, wherein the support element is twistedly foldable to a smaller diameter, (b) a flexible heart valve with a plurality of valvular leaflets releasably attached to the support element, and (c) a receptacle having a plurality of connecting members secured to the cylindrical support element, wherein the receptacle is releasably matched to an expanding element capable of matching and untwisting the receptacle that is adapted for un-twisting and unfolding the flexible heart valve.

As discussed above, the connecting bars 56 are secured to the intercrossing bars or stenting struts of the support element 51 either releasably or permanently. The connecting bars 56 are better secured to the heart valve structure far away from the moving valve leaflets with minimal interference to the valvular function. The connecting bars 56 are made of a biocompatible metallic material, sized and configured to minimize affecting the mounting and/or the function of the valvular structure or cusps 64. In one embodiment, the connecting bars 56 are coupled to the intercrossing bars (or stenting struts) securely with an appropriate manner and at a proper location of the intercrossing bars so as to untwist the cylindrical support essentially uniformly across all the stenting struts or intercrossing bars. The atrioventricular valves 50 comprise a plurality of cusps, each cusp having two generally straight side edges that are joined at a semicircular tip edge, wherein each of the straight side edges 59 is trimmed and configured at an angle of about 20 degrees or less, preferably between a range of 15 to 20 degrees, from a reference central longitudinal line 58 of the cusps. The intercrossing bars of the present invention may be conveniently substituted by any other stent strut configuration.

Supportless Heart Valve Prosthesis

Most conventional heart valves are manufactured as stented valves. The stented valve with tissue cusps or plastic cusps could be implanted percutaneously as discussed above with an untwist mechanism of the present invention. In the last few years, stentless heart valves with more flexible annular rings are available; however, those valves are still typically supported by sutures or clothes on the valve and/or between the cusps and the valve base. A commercially available pericardium valve made by suturing leaflets together to form a valve on a stent support is not a "supportless valve".

One embodiment of the "supportless" atrioventricular valves has been disclosed in a co-pending application Ser. No. 10/086,100 filed Feb. 28, 2002 entitled "Stentless atrioventricular heart valve fabricated from a singular flat membrane", entire contents of which are incorporated herein by reference. Specifically, the supportless valves comprise a plurality of cusps, each cusp having two generally straight side edges that are joined at a generally semicircular tip edge, wherein each of the straight side edges 59 is trimmed and configured at an angle of about 20 degrees or less, preferably between a range of 15 to 20 degrees, from a reference central longitudinal line 58 of the cusps 64. The atrioventricular valve has no additional support, such as a conventional stenting element made of metal or plastic material. A supportless atrioventricular valve 50A in FIG. 8 is quite feasible for delivery to an implant site by a minimally invasive manner.

An atrioventricular heart valve made of a singular flexible membrane has been disclosed in the co-pending application Ser. No. 10/086,100 filed Feb. 28, 2002. FIG. 8 shows a supportless sewing ring 63 with a trimmed membrane. In one illustration of a bi-leaflet valve, the periphery portion is trimmed and configured to include a plurality of cusps 64, such as a posterior cusp and an anterior cusp. The sewing ring 63 comprises an opening 62 defined by a perimeter including at least a first and a second straight side portions thereof. A circular, oval shaped or D-shaped ring opening that is supportless and flexible for replacing a dysfunctional atrioventricular valve is well known to a cardiac surgeon or skilled artisan. Each cusp 64 is configured hinged continuously from a straight side portion, wherein the cusps are an integral part of a continuum from the singular membrane with a common commissure.

In an illustrative embodiment, the sewing ring element 63 may be made of a biocompatible material selected from a group consisting of non-biodegradable plastic material, biodegradable plastic material, non-biodegradable biological material, or biodegradable biological material. The sewing ring element may be textured, porous, or constructed of fabric components suitable for valve fabrication. In a particular embodiment, the sewing ring element of the present invention may be a virtual element or a temporary template. The "virtual element" is herein intended to mean an imaginary non-existing element that aids in better describing and assisting the valve fabrication process as disclose in the co-pending application Ser. No. 10/086,100 filed Feb. 28, 2002.

The flexible heart valve may be selected from a biological tissue, a synthetic polymer or a synthetic protein matrix. The biological tissue may be chemically treated to reduce its antigenicity and/or immunogenicity. The chemicals for treating biological tissue may include glutaraldehyde, formaldehyde, dialdehyde starch, polyepoxy compounds, or the like that are well known to one who is skilled in the art of chemical treatment. Further, the tissue may be pericardium tissue selected from a group consisting of equine, bovine, porcine, ovine, human, or other animals. The thickness of tissue membrane is preferred to be in the range of less than 0.1 mm up to about a few millimeters. The singular membrane made of synthetic polymer may be selected from a group consisting of polyurethane, silicone, expanded polytetrafluoroethylene, fluoro-polymer, polyester, polyethylene, polypropylene, latex, co-polymer or mixture thereof. The singular membrane of the present invention has adequate strength or mechanical properties suitable as a heart valve construct.

The trimmed edges of the cusps 64 of the atrioventricular valves 50, 50A is trimmed and configured at an angle (θ) of about less than 20 degrees from a reference central longitudinal line 58. The angle θ may preferably be in the range of about 15 to 20 degrees.

As disclosed in the co-pending application Ser. No. 10/086,100 filed Feb. 28, 2002 entitled "Stentless atrioventricular heart valve fabricated from a singular flat membrane", entire contents of which are incorporated herein by reference, the distal portion of the cusp 64 may comprise texture elements (not shown) at edge portion(s) of the cusps configured to extend the texture element(s) for connection to papillary muscles in a ventricle cavity when the sewing ring is secured to an atrioventricular junction of a patient heart by a percutaneous procedure. For illustration purposes, the texture element may be made of silicone rubber (Silastic™), cloth (usually Dacron™), or cloth coated with polytetrafluoroethylene (Teflon™) or other fabric. A conventional method of securing the texture element onto the cusp may include bonding, stitching, gluing, suturing or the like.

In a co-pending patent application Ser. No. 09/853,463 filed May 10, 2001 entitled "Delivery System For A Stentless Valve Bioprosthesis" by applicants, entire contents of which are incorporated herein by reference, discloses an improved delivery system for delivering a stentless bioprosthesis in a minimally invasive manner.

As disclosed in a co-pending application Ser. No. 10/137,637 filed May 2, 2002 entitled "Supportless atrioventricular heart valve and minimally invasive delivery systems thereof", entire contents of which are incorporated herein by reference, a delivery means for minimally invasively deploying a medical device to the interior of a body through a percutaneous intercostal penetration. It is one object of the present invention to provide a method for minimally invasively delivering a foldable heart valve into a patient. The method comprises: folding the valve within a lumen of delivery means for delivering said valve to a target valvular annulus of the patient; and unfolding the valve in place by a balloon catheter, wherein a differentially expandable balloon of the balloon catheter is configured to expand the circularly folded valve into an oval unfolded valve. In one aspect of the present invention, the differentially expandable balloon comprises a longitudinal axis, a major traverse axis and a minor traverse axis, the major traverse axis being at least 10% longer than the minor traverse axis. In another aspect of the present invention, the differentially expandable balloon is delivered through a percutaneous intercostal penetration of the patient. The differentially expandable balloon may be delivered through an opening selected from a group consisting of a carotid artery, a jugular vein, a subclavian vein, and a body vessel.

The delivery apparatus 21 may be made from plastic material, metal or composite material. In one embodiment, the delivery apparatus may be made of the material selected from the group consisting of polyethylene, polypropylene, polycarbonate, nylon, polytetrafluoroethylene, polyurethane, stainless steel, Nitinol, titanium, polyimide, polyester, and the like.

The present invention discloses a method of forming a supportless atrioventricular valve intended for attaching to a circumferential valve ring and papillary muscles of a patient as afore-mentioned described. Furthermore, the present invention discloses a method for minimally invasively delivering a supportless atrioventricular valve made of a singular membrane of tissue into a patient, the method comprising folding the valve within a lumen of delivery means for delivering through a cardiac wall into a left atrium of the patient. The method may comprise the steps of (a) advancing a delivery apparatus of the delivery means through a percutaneous intercostal penetration and reaching the cardiac wall, wherein the delivery apparatus comprises a cup balloon at a distal section of the delivery apparatus having a plurality of suction ports at a balloon rim of said cup balloon; (b) deploying the cup balloon and applying suction to said plurality of suction ports to create an isolated enclosure around a distal region of the delivery apparatus; (c) introducing a sharp-end inner medical device inside said delivery apparatus toward the cardiac wall and creating a passthrough opening on said wall; (d) withdrawing the sharp-end inner medical device from said delivery apparatus; (e) introducing a second inner medical device having the folded supportless atrioventricular valve through the passthrough opening into the left atrium; and (f) delivering the atrioventricular valve suitable out of said second inner medical device for implanting at a heart valve location.

In operation, a delivery apparatus 21 of the present invention may be deployed through an intercostal penetration. The delivery apparatus may be introduced through a cannula or trocar positioned in one of percutaneous intercostal penetrations, the cannula or trocar having a proximal end disposed outside of the patient and a distal end disposed within the chest.

From the foregoing description, it should now be appreciated that a percutaneously deliverable heart valve suitable for replacement of diseased human heart valve and delivery means thereof have been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A method for minimally invasively delivering a foldable heart valve prosthesis into a patient, the foldable heart valve prosthesis comprising a twistedly foldable support element and a heart valve releasably secured to said support element, said method comprising:

twistedly folding said support element with the secured heart valve within a lumen of a delivery apparatus by twisting and folding said support element by compressing an expanding metallic frame with intercrossing linear bars;

delivering said delivery apparatus to a target valvular annulus of the patient; and un-twisting said support element to unfold and deploy said heart valve in place.

2. The method of claim 1, wherein the delivery apparatus comprises a catheter.

3. The method of claim 2, wherein the delivery step is carried out with said catheter through an opening selected from a group consisting of a carotid artery, a jugular vein, a subclavian vein, and a body vessel.

4. The method of claim 1, wherein the delivery apparatus comprises a cannula.

5. The method of claim 4, wherein the delivery step is carried out with said cannula through a percutaneous intercostal penetration.

6. The method of claim 5 further comprising a step of removing at least a portion of a patient's heart valve by means of a cutting tool introduced through the percutaneous intercostal penetration and through an internal penetration on a cardiac wall before the twistedly folding step.

7. The method of claim 5, wherein the step of removing is carried out by providing radiofrequency energy to the cutting tool.

8. The method of claim 5 further comprising a step of fastening the unfolded heart valve within the valvular annulus by means of an instrument introduced through the percutaneous intercostal penetration and through an internal penetration on a cardiac wall after the un-twisting step.

9. The method of claim 1 further comprising a step of removing the support element after the un-twisting step.

10. A twistedly foldable heart valve system to replace a diseased valve of a patient comprising:

a generally cylindrical support element with a diameter, the support element further comprising an expanding metallic frame with intercrossing linear bars, wherein the support element is twistedly foldable and compressible to a smaller diameter;

a flexible heart valve with a plurality of valvular leaflets releasably attached to said support element; and a receptacle having a plurality of connecting members secured to the cylindrical support element, wherein the receptacle is releasably attached and matched to an expanding element, the expanding element further being capable of matching and untwisting the receptacle adapted for un-twisting and unfolding said heart valve.

11. The heart valve system of claim 10, wherein the flexible heart valve is made of tissue material.

12. The heart valve system of claim 11, wherein the tissue material is pericardium tissue selected from a group consisting of equine, bovine, porcine, and ovine.

13. The heart valve system of claim 11, wherein the tissue material is chemically treated to reduce antigenicity of said tissue material.

14. The heart valve system of claim 13, wherein the tissue material is chemically treated with a chemical selected from a group consisting of glutaraldehyde, formaldehyde, dialdehyde starch, and polyepoxy compounds.

15. The heart valve prosthesis of claim 10, wherein the flexible heart valve is made of a material selected from a polymer group consisting of silicone, polyurethane, latex, and mixture thereof.

16. The heart valve system of claim 10, wherein the cylindrical support element further comprises a plurality of anchoring members for anchoring said support element onto annular tissue of the diseased valve.

17. The heart valve system of claim 16, wherein the anchoring members are triggered for facing outwardly when the support element is untwisted.

18. The heart valve system of claim 10, wherein the diseased valve is an aortic valve.

19. The heart valve prosthesis of claim 10, wherein the diseased valve is a pulmonary valve.

20. The heart valve prosthesis of claim 10, wherein the diseased valve is an atrioventricular valve.

21. The heart valve system of claim 11, wherein said flexible heart valve is an atrioventricular valve comprising a plurality of cusps, each cusp having a semicircular tip edge and two generally straight side edges that are joined at said semicircular tip edge, wherein each of said straight side edges is trimmed and configured at an angle of about less than 20 degrees from a reference central longitudinal line of said cusp.

22. The heart valve system of claim 10, wherein the expanding element is made of a material selected from a group consisting of polyethylene, polypropylene, polycarbonate, nylon, polytetrafluoroethylene, polyurethane, stainless steel, Nitinol, titanium, polyimide, polyester, and mixture thereof.

23. The heart valve system of claim 10, wherein the support element is made of a material selected from a group consisting of stainless steel, Nitinol, titanium, gold, and shape-memory material.

24. A twistedly foldable heart valve system to replace a diseased valve of a patient comprising:

a generally cylindrical support element with a diameter, wherein the support element is twistedly foldable and compressible to a smaller diameter;

a flexible heart valve with a plurality of valvular leaflets releasably attached to said support element; and a receptacle having a plurality of connecting members secured to the cylindrical support element, wherein the receptacle is releasably attached and matched to an expanding element, the expanding element further being capable of matching and untwisting the receptacle adapted for un-twisting and unfolding said heart valve;

wherein the flexible heart valve is made of tissue material;

wherein said flexible heart valve is an atrioventricular valve comprising a plurality of cusps, each cusp having a semicircular tip edge and two generally straight side edges that are joined at said semicircular tip edge, wherein each of said straight side edges is trimmed and configured at an angle of about less than 20 degrees from a reference central longitudinal line of said cusp.

* * * * *